United States Patent
Lu (10) Patent No.: US 11,179,338 B1
(45) Date of Patent: Nov. 23, 2021

(54) POWDER FOR ORAL SUSPENSION CONTAINING TADALAFIL

(71) Applicant: AUSON PHARMACEUTICALS INC., Bridgewater, NJ (US)

(72) Inventor: Enxian Lu, Bridgewater, NJ (US)

(73) Assignee: AUSON PHARMACEUTICALS INC., Bridgewater, NJ (US)

( * ) Notice: Subject to any disclaimer, the term of this patent is extended or adjusted under 35 U.S.C. 154(b) by 0 days.

(21) Appl. No.: 17/237,319

(22) Filed: Apr. 22, 2021

Related U.S. Application Data (63) Continuation-in-part of application No. PCT/US2021/026636, filed on Apr. 9, 2021.

(51) Int. Cl.
  *A61K 9/50* (2006.01)
  *A61K 9/16* (2006.01)
  *A61K 9/00* (2006.01)
  *A61K 31/4985* (2006.01)

(52) U.S. Cl.
  CPC .......... *A61K 9/1652* (2013.01); *A61K 9/0053* (2013.01); *A61K 9/1611* (2013.01); *A61K 9/1623* (2013.01); *A61K 31/4985* (2013.01)

(58) Field of Classification Search
  None
  See application file for complete search history.

(56) References Cited

U.S. PATENT DOCUMENTS

| | | | |
|---|---|---|---|
| 2016/0000720 A1* | 1/2016 | Bhavanasi | B29C 37/0025 424/489 |
| 2017/0326139 A1* | 11/2017 | Foster | A61K 31/18 |
| 2021/0052591 A1* | 2/2021 | Pandya | A61K 9/0095 |

FOREIGN PATENT DOCUMENTS

| | | |
|---|---|---|
| EP | 3510997 A1 | 7/2019 |
| WO | 2011/030351 A2 | 3/2011 |
| WO | 2019/130052 A1 | 7/2019 |

OTHER PUBLICATIONS

Waterman et al. "Accelerated aging: Prediction of chemical stability of pharmaceuticals" (2005) International journal of pharmaceutics. 293. 101-25. 10.1016/j.ijpharm.2004.12.013.
International Search Report and Written Opinion dated Jul. 8, 2021, for related International Application No. PCT/US21/26636, 9 pages.

* cited by examiner

*Primary Examiner* — Susan T Tran
(74) *Attorney, Agent, or Firm* — Fox Rothschild LLP (57) ABSTRACT

This document discloses a powder formulation of tadalafil for oral administration. Also disclosed are a method of preparing the powder formulation, a suspension dosage form of tadalafil and a method of treating diseases.

19 Claims, 2 Drawing Sheets

POWDER FOR ORAL SUSPENSION CONTAINING TADALAFIL

FIELD OF THE INVENTION

This patent document discloses a novel formulation of tadalafil or its pharmaceutically acceptable salt, a method for its preparation and its use in medical therapy.

BACKGROUND

Tadalafil is marketed in the United States by Eli Lilly and Company, under the trade name Cialis and Adcirca. Cialis is for the indication of erectile dysfunction and Adcirca is for the indication of pulmonary arterial hypertension (PAH), both are immediate release tablets. As a result, hospital pharmacists are often required to compound liquid formulations using crushed tadalafil tablets for pediatric patients and patients who cannot swallow tablets. A need exists for an improved formulation of Tadalafil.

SUMMARY

The powder formulation described herein allows for convenient oral administration of Tadalafil. The formulation resolved the dose inaccuracy issue due to the precipitation of crushed tadalafil tablets in a suspension system. Further, the formulation substantially improves the stability and dose accuracy of the medication.

An aspect of this patent document provides a powder formulation suitable for reconstitution with a pharmaceutically acceptable carrier to form a stable suspension oral dosage form. The formulation contains tadalafil or a pharmaceutically acceptable salt thereof and a suspending agent. The suspending agent is effective for maintaining a sedimentation volume ratio of more than about 0.8 for at least 24 hours after the powder formulation is reconstituted into an aqueous suspension.

In some embodiments, less than about 0.5% of the tadalafil or the pharmaceutically acceptable salt thereof decomposes for about 3 months after the powder formulation is reconstituted into the suspension.

In some embodiments, tadalafil or a pharmaceutically acceptable salt is in an amount of 1 mg/ml to 50 mg/ml after the powder formulation is reconstituted into the suspension. In some embodiments, the amount is 5 mg/ml.

In some embodiments, the suspending agent is in an amount of 0.5 mg/ml to 8 mg/ml after the powder formulation is reconstituted into the suspension. In some embodiments, the amount is 4 mg/ml.

In some embodiments, the tadalafil or the pharmaceutically acceptable salt thereof and the suspending agent have a ratio ranging from about 5:0.5 to about 5:8 by weight. In some embodiments, the ratio is about 5:4 by weight.

In some embodiments, the suspending agent is selected from the group consisting of hydrocolloid gum, cellulosic derivative, a polysaccharide, alginate, acrylic acid copolymer, Polyvinylpyrrolidone, aluminiummagnesium silicate, and any combination thereof. In some embodiments, the suspending agent is hydrocolloid gum. In some embodiments, the suspending agent is xanthan gum.

In some embodiments, the sedimentation volume ratio remains more than about 0.8 within 24 hours after the powder formulation is reconstituted into the suspension. In some embodiments, the suspension is achieved within about 3 minutes after the powder formulation is reconstituted with water. In some embodiments, the suspension is homogeneous.

In some embodiments, the suspension provides an in vitro release of at least about 75% of the tadalafil after 10 minutes (USP dissolution apparatus 2, in 1000 ml of 0.5% SLS at 50 rpm). In some embodiments, the powder formulation after being reconstituted into the suspension provides a release of the tadalafil bioequivalent to Adcirca tablet of the same dose. In some embodiments, the suspension prepared from the powder formulation provides a release of the tadalafil bioequivalent to a non-suspension dosage form (e.g. Adcirca tablet), which provides a therapeutically effective blood concentration of tadalafil.

In some embodiments, the tadalafil or the pharmaceutically acceptable salt thereof has a D90 ranging from about 1 μm to about 20 μm prior to being mixed with the suspending agent.

In some embodiments, the formulation further contains glidants including for example silicon dioxide, starch, talc and any combination thereof in about 0% to about 10%. In some embodiments, the glidant is silicon dioxide. In some embodiments, silicon dioxide amount is about 2.5%.

In some embodiments, the formulation further contains a diluent selected from the group consisting of sucrose, dextrose, mannitol, sorbitol, maltitol, starch, lactose, microcrystalline cellulose, and any combination thereof in about 10% to about 98% by weight of the powder formulation. In some embodiments, the diluent is sorbitol.

In some embodiments, the formulation further contains a buffering agent selected from the group consisting of sodium citrate, citric acid, fumaric acid, tartaric acid, potassium citrate, sodium bicarbonate, potassium bicarbonate, sodium dihydrogen phosphate, disodium hydrogen phosphate, sodium hydroxide and potassium dihydrogen phosphate.

In some embodiments, the formulation further contains a preservative selected from the group consisting of Methyl Paraben or its sodium salt, Ethyl Paraben or its sodium salt, Propyl Paraben or its sodium salt, Sodium Benzoate, benzoic acid, Sorbic Acid, potassium sorbate, propionic acid and any combination thereof in about 0% to about 10%.

In some embodiments, the reconstituted suspension has a pH in the range of 2 to 6 after the powder formulation is reconstituted into the suspension.

In some embodiments, the reconstituted suspension is easily pourable and has a viscosity in the range of 10 to 5000 cP at 25° C.

Another aspect provides a method of preparing the powder formulation disclosed herein. The method includes
(a) mixing tadalafil or a pharmaceutically acceptable salt thereof with a first portion of glidant to obtain a first mixture; and
(b) mixing the first mixture with one or more additional excipients.

In some embodiments, the method further includes mixing the first mixture with a first portion of diluent prior to step (b). In some embodiments, the method further includes mixing the first mixture, during step (b) or after step (b) with a second portion of the glidant and/or a second portion of diluent. In some embodiments, the glidant is silicon dioxide and the diluent is sorbitol.

Another aspect of the invention provides a suspension including tadalafil or a pharmaceutically acceptable salt thereof or a derivative thereof and a suspending agent. The suspension maintains a sedimentation volume ratio of more than about 0.8 for at least 24 hours after the suspension is prepared. In some embodiments, the suspension can be prepared from the above described powder formulation by reconstitution or by mixing the necessary components in suitable means as long as the resulting suspension achieves a desirable profile for oral administration.

In some embodiments, the ratio between the tadalafil (or a pharmaceutically acceptable salt thereof or a derivative thereof) and the suspending agent in the suspension ranges from about 10:1 to about 5:8 by weight. In some embodiments, the ratio is about 5:4 by weight. In some embodiments, the suspending agent is hydrocolloid gum. In some embodiments, the suspending agent is xanthan gum.

In some embodiments, the ratio of area under curve (AUC 0-inf) between tadalafil suspension to Adcirca tablet with the same dose is between 0.8 to 1.25 after oral administration. In some embodiments, the ratio of a maximum tadalafil plasma concentration (Cmax) between tadalafil suspension to Adcirca tablet with the same dose is between 0.7 to 1.20 after oral administration.

In some embodiments, the plasma concentration profile at steady state is characterized by a maximum tadalafil plasma concentration to average plasma concentration ratio (Cmax/Cave) of about 1.4 to 1.9 after administration.

In some embodiments, the plasma concentration profile at steady state is further characterized by a minimum tadalafil plasma concentration to average plasma concentration ratio (Cmin/Cave) of about 0.5 to 0.8 after administration.

Another aspect of the patent document provides a method of treating a disease comprising administering the suspension described herein to a subject in need, wherein the disease is selected from the group consisting of erectile dysfunction, enlarged prostate and pulmonary arterial hypertension. Other exemplary applications include treatment of Heart failure, hypertension, Left ventricle diastolic dysfunction, scleroderma spectrum of disease, Systemic Sclerosis, Raynaud's, fetal growth restriction, Mountain Sickness, Skeletal Muscle and Perceptual Fatigue, Interstitial Lung Disease of Scleroderma, Chronic Obstructive Pulmonary Disease, Duchenne Muscular Dystrophy.

DETAILED DESCRIPTION

This document discloses a powder formulation suitable for reconstitution with a pharmaceutically acceptable carrier to form a suspension oral dosage form of tadalafil. Advantages of the powder formulation and dosage form include prolonged stability, dose titration accuracy and better compliance in comparison with conventional immediate release non-suspension dosage forms.

Tadalafil is known as pyrazino [1',2':1,6]pyrido[3,4-b]indole-1,4-dione, 6-(1,3-benzodioxol-5-yl) 2,3,6,7,12,12a-hexahydro-2-methyl-, (6R,12aR)-. Tadalafil is insoluble in water. When crushed tadalafil tablets are simply added directly into water or other soft food, the compound tends to settle rapidly and cannot be easily redistributed and as such would potentially affect the dose accuracy delivered to a patient.

The powder formulation and suspension dosage form disclosed herein effectively resolved the above issues. After reconstitution, the uniform liquid suspension enables easy and accurate dose titration with an improved taste. The powder formulation and suspension dosage form described in this patent document are applicable to Tadalafil as well as salts, isomers, complexes, polymorphs, hydrates, esters and prodrugs thereof.

While the following text may reference or exemplify specific embodiments of a dosage form or a method of manufacturing the dosage from, it is not intended to limit the scope of the dosage form to such particular reference or examples. Various modifications may be made by those skilled in the art, in view of practical and economic considerations, such as the amount of individual excipients and the manufacturing condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "about" as used herein refers to the referenced numeric indication plus or minus 10% of that referenced numeric indication.

The term "active ingredient" or "active pharmaceutical ingredient" (API) refers to a compound (e.g. tadalafil) that can be used for treating a disorder or condition in a subject (e.g., a patient), or for preventing one or more symptoms of such disorder or condition in the subject.

The term "bioequivalence" or "bioequivalent" refers to two formulations, dosage forms, products, or compositions of an active ingredient having biological equivalence. It is generally considered bioequivalent if the 90% Confidence Interval ("CI") of the relative mean Cmax, AUC(0-t) and AUC(0-∞) of the test formulation to reference formulation (i.e., brand product) is within 80.0% to 125.0% in the fasting state of a tested subject.

The term "patient compliance" refers to the degree to which patient correctly follows medical advice.

The term "excipient" refers to any inert substance that may have specific functions to the active ingredient (e.g., swelling agent, controlling-release, osmotic agent). An excipient provides without limitation, bulk, consistency, stability, binding ability, lubrication, disintegrating ability, etc., to the formulation of an active ingredient. A "suspending agent" is a type of excipient. An excipient may function for multiple purposes.

The term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The term "pharmaceutically acceptable salts" means salts of tadalafil which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "powder" as used herein refers to any composition or formulation which is dry and flowable. Non-limiting examples include granules, flakes, spheroids and other forms which can be readily prepared and mixed with an ingestible liquid to provide a desirable liquid suspension.

The term "wet granulation" refers to a process of using a liquid binder to lightly agglomerate the powder mixture.

The term "release", "released", "releasing", and the like, when used in connection with a pharmaceutical compression or dosage form, refers to the process or the portion of the active ingredient that leaves the dosage form following contact with an aqueous environment. Unless otherwise indicated, the quantity of an active ingredient released from a dosage form is measured by dissolution testing in water as described in this invention. The results of the dissolution testing are reported as % (w/w) released as a function of time or as the release time. In some embodiments, complete release of an active ingredient occurs when at least 90% of the active ingredient has been released from the dosage form.

The term "immediate-release" refers to those which disintegrate rapidly and/or get dissolved to release the medicaments or active ingredient. For example, more than or equal to about 85% or more than or equal to about 90% of an active pharmaceutical ingredient in an immediate release dosage form is released in less than or equal to about 1 hour. In some embodiments, more than or equal to about 80% or more than or equal to about 90% or more than or equal to about 95% of an active pharmaceutical ingredient in an immediate release dosage form is released in less than or equal to about 30 minutes.

The term "Cmax" or "peak plasma exposure", expressed in ng/mL, refers to the point of maximum concentration of drug in plasma.

The term "area under curve (AUC)" or "total plasma exposure", expressed in µg·hr/mL, refers to the total integrated area under plasma level time profile and expresses the total amount of the active ingredient that comes into systemic circulation after administration.

The term "D90" refers to the particle size corresponding to 90% of the cumulative undersize distribution by volume.

The term "pharmaceutically acceptable excipient or carrier" refers to an agent or a substance that enable an active ingredient or a composition thereof to be formulated as tablets, pills, dragees, capsules, liquids, gels, syrups, slurries, suspensions and the like, for administration to a subject in need.

The term "sedimentation volume ratio" or "sedimentation ratio" refers to a ratio of the ultimate volume of sediment (Vu) to the original volume of sediment (VO) before settling.

The term "subject" refers to a mammal, such as an animal or a human. Hence, the methods disclosed herein can be useful in human therapy and veterinary applications. In one embodiment, the subject is an animal. In another embodiment, the subject is a human.

The term "treat" or "treating" refers to attain or attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a patient suffering from the condition, decreasing the dose of another medication required to treat the condition, enhancing the effect of another medication a patient is taking for the condition, and prolonging the survival of a patient having the condition.

An aspect of the document provides a powder formulation suitable for reconstitution with a pharmaceutically acceptable carrier to form a stable suspension oral dosage form of tadalafil. The formulation includes:

tadalafil, a pharmaceutically acceptable salt, an isomers, a complex, a polymorphs, a hydrate, or an ester thereof;

a suspending agent in an amount ranging from about 0.1% to about 10% w/w based on the total weight of the formulation.

In some embodiments, the suspending agent, other excipients, and their respective amounts are selected so that they are effective for maintaining a sedimentation volume ratio of more than about 0.7, more than about 0.8, more than about 0.9, or more than about 0.95 for a period of at least 12 hours, at least 24 hours, at least 48 hours, at least 3 days, at least 5 days, at least 7 days, or at least 2 weeks after the powder formulation is reconstituted into a suspension.

In some embodiments, the pharmaceutically acceptable carrier is water or an aqueous solution containing one or more agents or excipients. The salt of tadalafil includes for example HCl salt, salicylate salt, citrate salt and mandelate salt.

The amount of the suspending agent in the formulation can vary depending on factors such as the dosage of tadalafil and the specific suspending agent.

In some embodiments, the suspending agent is in an amount ranging from about 1% to about 8%, from about 1.5% to about 6%, from about 2% to about 5%, or from about 2.5% to about 4%, w/w in the powder formulation. Non-limiting examples include about 1%, about 1.2%, about 1.4%, about 1.8%, about 2%, about 2.2%, about 2.4%, about 2.5%, about 2.6%, about 2.8%, about 3%, about 3.5%, about 4%, about 4.5%, about 5%, about 5.5%, about 6%, about 7%, or about 8%. In some embodiments, the suspending agent is xanthan gum.

In some embodiments, the suspending agent is in an amount of from 0.5 mg/ml to 10 mg/ml, from 0.5 mg/ml to 8 mg/ml, from 0.5 mg/ml to 6 mg/ml, after the powder formulation is reconstituted into the suspension. In exemplary embodiments, the amount is about 2, about 3, about 4, about 5, or about 6 mg/ml after the powder formulation is reconstituted into the suspension.

The suspending agent stabilizes the resulting suspension for an extended period of time after the formulation is reconstituted with for example water or an aqueous solution.

Various mechanical means, such as shaking, swirling, heating, or any combination thereof can be used to promote a uniform suspension.

The suspending agent contributes to the stability of the suspension after reconstitution. In some embodiments, the suspending agent and its amount are selected so that the suspension maintains a sedimentation ratio of more than 0.8, more than 0.9, more than 0.95, or more than 0.98 for a period of at least 10 minutes, at least 20 minutes, at least 20 minutes, at least 1 hour, at least 2 hours, at least 4 hour, at least 8 hours, at least 12 hours, at least 24 hours, or at least 48 hours. In some embodiments, the suspending agent, the one or more pharmaceutically acceptable excipients, and their respective amounts are selected so that less than about 5%, less than about 3%, less than about 1%, less than about 0.5%, less than about 0.2%, or less than about 0.1% of the tadalafil or a pharmaceutically acceptable salt thereof is decomposed for a period of at least 6 months, at least 5 months, at least 4 months, at least 3 months, at least 2 months, at least 1 month, at least 3 weeks, at least 2 weeks or at least 1 week after the formulation is reconstituted into a suspension.

The ratio between tadalafil (or a pharmaceutically acceptable salt thereof) and the suspending agent ranges from about 40:1 to about 1:10 by weight. In some embodiments, the ratio ranges from about 30:1 to about 1:5, from about 20:1 to about 2:5, from about 10:1 to about 1:1 or from about 5:2 to about 5:6. Non-limiting examples of the ratio between tadalafil (or a pharmaceutically acceptable salt thereof) and the suspending agent include about 10:2, about 10:3, about 10:4, about 10:5, about 10:6, about 10:7, about 10:8, about 10:9, about 10:10, about 10:11, about 10:12, about 10:13, about 10:14, and about 10:15.

Non-limiting examples of the suspending agent include hydrocolloid gums such as xanthan gum, guar gum, locust-bean gum, gum tragacanth, veegum, sodium alginate, carrageenan; cellulosic derivatives such as sodium carboxymethylcellulose, hydroxypropyl cellulose, methyl cellulose, hydroxypropyl methylcellulose; polysaccharides such as starch and pregelatinised starch; alginates such as sodium alginate; acrylic acid copolymers such as carbopols; Polyvinylpyrrolidone; aluminiummagnesium silicate; and combinations thereof. In some embodiments, the suspending agent is hydrocolloid gum. In some embodiments, the suspending agent is xanthan gum.

The powder formulation after reconstitution into a suspension provides an in vitro release as measured by USP dissolution apparatus 2. In some embodiments, at least about 95%, at least about 90%, at least about 85%, at least about 80%, at least about 75%, at least about 65% or at least about 50% of the tadalafil is released in a medium of 0.5% sodium lauryl sulphate (SLS) after 10 minutes (USP dissolution apparatus 2, in 1000 ml of 0.5% SLS at 50 rpm).

The power formulation can also provide a release of tadalafil bioequivalent to non-suspension formulation of tadalafil at the same dose. Examples of non-suspension formulation of tadalafil include tadalafil tablets. In some embodiments, the dose of tadalafil in the formulation ranges from about 2 mg to about 50 mg, including for example about 2.5 mg, about 5 mg, about 10 mg, about 20 mg, about 40 mg and about 80 mg.

The tadalafil or the pharmaceutically acceptable salt thereof or the derivative thereof used for the preparation of the powder formulation has a D90 of less than about 80 µm, less than about 70 µm, less than about 60 µm, less than about 50 µm, less than about 40 µm, less than about 30 µm, less than about 20 µm, less than about 10 µm. In some embodiments, the D90 ranges from about 3 µm to about 40 µm, from about 2 µm to about 30 µm, from about 1 µm to about 20 µm, or from about 0.5 µm to about 10 µm.

The formulation can contain one or more additional carrier or excipient including for example, surface active agents, sweeteners, lubricants, glidants, diluents, smoothing agents, suspension agents, film forming substances, buffering agents and coating assistants, or a combination thereof. In some embodiments, the formulation further contains a diluent including for example sucrose, dextrose, mannitol, sorbitol, maltitol, starch, lactose, microcrystalline cellulose, and any combination thereof in about 10% to about 98% by weight of the powder formulation.

In some embodiments, the formulation further contains a diluent (e.g. sorbitol) ranging from about 50% to about 85% or from about 70% to about 80% by weight in the powder formulation. Non-limiting examples of the amount of the diluent (e.g. sorbitol) in the formulation include about 55%, about 60%, about 65%, about 68%, about 70%, about 72%, about 75%, about 78%, about 80%, about 82%, about 84%, and 86%.

In some embodiments, the formulation further contains glidants including for example silicon dioxide, starch, talc and any combination thereof ranging from about 0.1% to about 10%, from about 1% to about 6%, preferably from about 2% to about 5% from about 1% to about 3.5%, or from about 2% to about 2.5%. Exemplary amounts of glidant include 0.5%, 0.8%, 1%, 1.5%, 1.8%, 2%, 2.5%, 3%, 3.5%, and 4% by weight in the formulation. In some embodiments, the glidant is silicon dioxide.

In some embodiments, the formulation further contains a preservative selected from the group consisting of Methyl Paraben or its sodium salt, Ethyl Paraben or its sodium salt, Propyl Paraben or its sodium salt, Sodium Benzoate, benzoic acid, Sorbic Acid, potassium sorbate, propionic acid and any combination thereof in about 0% to about 10%.

In some embodiments, the formulation further contains a buffering agent including for example sodium citrate, citric acid, fumaric acid, tartaric acid, potassium citrate, sodium bicarbonate, potassium bicarbonate, sodium dihydrogen phosphate, disodium hydrogen phosphate, sodium hydroxide and potassium dihydrogen phosphate. The buffer concentration after reconstitution of the powder formulation into a suspension ranges from about 10 mM to about 200 mM, from about 10 mM to about 100 mM, or from about 10 mM to about 50 mM In some embodiments, the pH of the suspension ranges from about 1 to about 7, from about 2 to about 6 or from about 2.8 to about 4.8.

In some embodiments, the reconstituted suspension is easily pourable and has a viscosity in the range of 10 to 5000 cP at 25° C. In some embodiments, the viscosity is in the range from about 20 to 4000 cP at 25° C., from about 30 to 3000 cP at 25° C., from about 40 to 2000 cP at 25° C. Non-limiting examples of viscosity including 60, 80, 100, 150, 200, 400, 400, 500, 600, 700, 800, 1000, 1200, 1400, 1600, and 1800 cp.

In some embodiments, the formulation further contains a sweetener. Non-limiting examples include sucrose, glucose, sorbitol, sucralose, aspartame, saccharin sodium and any other pharmaceutically acceptable sweetener or combination thereof. The amount of the sweetener used in the powder for oral suspension compositions is typically in the range of from about 0.5% to about 10% w/w based on the total weight of the powder formulation.

In some embodiments, the formulation further contains a flavor. Non-limiting examples include grenadine flavor, berry flavor, strawberry flavor, banana flavor, orange flavor and peppermint flavor. The amount of the flavor in the powder for oral suspension is between about 0.1% to about 5% w/w based on the total weight of the powder formulation.

In some embodiments, the suspending agent, the one or more pharmaceutically acceptable excipients, and their respective amounts are selected so that the suspension prepared from the powder formulation provides a release of the tadalafil bioequivalent to the same dose of tadalafil in immediate release tablet form. In some embodiments, the suspending agent, the one or more pharmaceutically acceptable excipients, and their respective amounts are selected so that the ratio of area under curve (AUC 0-inf) between tadalafil suspension to tadalafil in immediate release tablet form with the same dose ranges from about 0.8 to about 1.25, preferably from about 0.9 to about 1.1, after oral administration. Non-limiting examples of the ratio include about 0.85, about 0.9, about 0.95, about 1, about 1.1, about 1.3, and about 1.5.

In some embodiments, the suspending agent, the one or more pharmaceutically acceptable excipients, and their respective amounts are selected so that the ratio of a maximum tadalafil plasma concentration (Cmax) between tadalafil suspension to tadalafil in immediate release tablet form with the same dose ranges from about 0.7 to about 1.20, preferably from about 0.75 to about 0.90, after oral administration. Non-limiting examples of the ratio include about 0.8, about 0.85, about 0.9, about 0.95, about 1, about 1.05, about 1.1, and about 1.5.

In some embodiments, the suspending agent, the one or more pharmaceutically acceptable excipients, and their respective amounts are selected so that the plasma concentration profile at steady state is characterized by a maximum tadalafil plasma concentration to average plasma concentration ratio (Cmax/Cave) ranging from about 1.4 to about 1.9, preferably from about 1.45 to about 1.65, after administration. Non-limiting examples of the ratio include about 1.5, about 1.55, about 1.6, about 1.7 and about 1.8.

In some embodiments, the suspending agent, the one or more pharmaceutically acceptable excipients, and their respective amounts are selected so that the plasma concentration profile at steady state is characterized by a minimum tadalafil plasma concentration to average plasma concentration ratio (Cmin/Cave) ranging from about 0.5 to about 0.8, preferably from about 0.6 to about 0.7, after administration. Non-limiting examples of the ratio include about 0.55, about 0.6, about 0.65, about 0.7, and about 0.8.

Another aspect of this patent document discloses a suspension including (a) tadalafil or a pharmaceutically acceptable salt thereof or a derivative thereof; and (b) a suspending agent, wherein the suspending agent is effective to keep the stable suspension after the suspension is prepared.

The ratio between the tadalafil (or a pharmaceutically acceptable salt thereof or a derivative thereof) and the suspending agent in the suspension is the same as in the above described formulation. In some embodiments, the ratio ranges from about 40:1 to abut 1:10 or from about 20:1 to about 1:2 by weight. In some embodiments, the ratio is about 5:4 by weight.

In some embodiments, the ratio ranges from about 30:1 to about 1:5, from about 20:1 to about 2:5, from about 10:1 to about 1:1 or from about 5:2 to about 5:6. Non-limiting examples of the ratio between tadalafil (or a pharmaceutically acceptable salt thereof) and the suspending agent include about 10:2, about 10:3, about 10:4, about 10:5, about 10:6, about 10:7, about 10:8, about 10:9, about 10:10, about 10:11, about 10:12, about 10:13, about 10:14, and about 10:15.

The particle size of the tadalafil, the suspending agent and other excipients (e.g. diluent, buffering agent) are also as described above. In some embodiments, the suspending agent is hydrocolloid gum. In some embodiments, the suspending agent is xanthan gum. Other excipients or carriers can be added to the suspension in any suitable sequence.

The concentration of the tadalafil (or a pharmaceutically acceptable salt thereof or a derivative thereof) in the suspension is in the range of from about 1 to about 50 mg/ml, from about 1 to about 20 mg/ml, or from about 1 to 15 mg/ml. In some embodiments, the concentration is 2, 3, 4, 5, 6, 8, 10, 15 or 20 mg/ml.

The concentration of the suspending agent in the suspension is in the range of from about 0.1 mg/ml to about 20 mg/ml, from about 0.2 mg/ml to about 10 mg/ml, from about 0.5 mg/ml to about 8 mg/ml, from about 1 mg/ml to about 6 mg/ml. Non-limiting examples of the concentration of the suspending agent in the suspension include 1, 2, 3, 4, 5, 6, 7, 8 and 9 mg/ml. Examples of the suspending agent are as described above. In some embodiments, the suspending agent is xanthan gum.

In some embodiments, the suspending agent is in an amount of from 0.5 mg/ml to 10 mg/ml, from 0.5 mg/ml to 8 mg/ml, from 0.5 mg/ml to 6 mg/ml, from 2.5 mg/ml to 6 mg/ml, from 3 mg/ml to 5 mg/ml, or from 3 mg/ml to 4 mg/ml in the suspension. In exemplary embodiments, the suspending agent is in an amount of about 2, about 2.5, about 3, about 3.5, about 4, about 4.5, about 5, or about 6 mg/ml in the suspension.

In some embodiments, the suspending agent and its amount are selected so that the suspension maintains a sedimentation ratio of more than 0.8, more than 0.9, more than 0.95, or more than 0.98 for a period of at least 10 minutes, at least 20 minutes, at least 20 minutes, at least 1 hour, at least 2 hours, at least 4 hour, at least 8 hours, at least 12 hours, at least 24 hours, or at least 48 hours. In some embodiments, the suspending agent, the one or more pharmaceutically acceptable excipients, and their respective amounts are selected so that less than about 5%, less than about 3%, less than about 1%, less than about 0.5%, less than about 0.2%, or less than about 0.1% of the tadalafil or a pharmaceutically acceptable salt thereof is decomposed for a period of at least 6 months, at least 5 months, at least 4 months, at least 3 months, at least 2 months, at least 1 month, at least 3 weeks, or at least 2 weeks.

In some embodiments, at least about 95%, at least about 90%, at least about 85%, at least about 80%, at least about 75%, at least about 65% or at least about 50% of the tadalafil is released in a medium of 0.5% sodium lauryl sulphate (SLS) after 10 minutes (USP dissolution apparatus 2, in 1000 ml of 0.5% SLS at 50 rpm).

The scope and examples of various excipients and their amounts are as described above. In some embodiments, the suspending agent, the one or more pharmaceutically acceptable excipients, and their respective amounts are selected so that the suspension provides a release of the tadalafil bioequivalent to the same dose of tadalafil in immediate release tablet form. In some embodiments, the suspending agent, the one or more pharmaceutically acceptable excipients, and their respective amounts are selected so that the ratio of area under curve (AUC 0-inf) between tadalafil suspension to tadalafil in immediate release tablet form with the same dose ranges from about 0.8 to about 1.25, preferably from about 0.9 to about 1.1, after oral administration. Non-limiting examples of the ratio include about 0.85, about 0.9, about 0.95, about 1, and about 1.5.

In some embodiments, the suspending agent, the one or more pharmaceutically acceptable excipients, and their respective amounts are selected so that the ratio of a maximum tadalafil plasma concentration (Cmax) between tadalafil suspension to tadalafil in immediate release tablet form with the same dose ranges from about 0.7 to about 1.20, preferably from about 0.75 to about 0.90, after oral administration. Non-limiting examples of the ratio include about 0.8, about 0.85, about 0.9, about 0.95, about 1, about 1.05, about 1.1, and about 1.5.

In some embodiments, the suspending agent, the one or more pharmaceutically acceptable excipients, and their respective amounts are selected so that the plasma concentration profile at steady state is characterized by a maximum tadalafil plasma concentration to average plasma concentration ratio (Cmax/Cave) ranging from about 1.4 to about 1.9, preferably from about 1.45 to about 1.65, after administration. Non-limiting examples of the ratio include about 1.5, about 1.52, about 1.55, about 1.56, about 1.58, about 1.6, about 1.62, about 1.65, about 1.7, about 1.75, and about 1.8.

In some embodiments, the suspending agent, the one or more pharmaceutically acceptable excipients, and their respective amounts are selected so that the plasma concentration profile at steady state is characterized by a minimum tadalafil plasma concentration to average plasma concentration ratio (Cmin/Cave) ranging from about 0.5 to about 0.8, preferably from about 0.6 to about 0.7, after administration. Non-limiting examples of the ratio include about 0.55, about 0.6, about 0.62, about 0.65, about 0.66, about 0.68, about 0.7, and about 0.8.

The suspension can be prepared from the above described powder formulation by reconstitution or by mixing the necessary components in suitable means as long as the resulting suspension achieves a desirable profile for oral administration. For example, the suspension can be prepared by adding a pre-calculated amount of water to the above described powder formulation containing suitable dosage of tadalafil or its salt and thoroughly mix the combined substances. By using a measuring cup or a syringe, a precise dosage can be obtained for oral administration. In exemplary embodiments, the powder formulation can be supplied in vials or bottles for multiple use or in unit dosage sachets for single use. In some embodiments, the powder formulation after reconstitution with water provides a liquid suspension containing 50 mg of tadalafil per 10 ml of liquid suspension.

The excellent stability of the powder formulation and the suspension allows for accurate dose titration and easy administration. This is especially important for pediatric patients and patients with dysphagia who cannot swallow tablets due to its size.

Another aspect of the patent document provides a method of preparing the above described formulation. The method generally includes mixing the tadalafil (or a pharmaceutically acceptable salt thereof or a derivative thereof), the suspending agent and other excipients. The ratio between the tadalafil (or a pharmaceutically acceptable salt thereof or a derivative thereof) and the suspending agent in the suspension is the same as in the above described formulation. The amounts of other excipients are as described above. Additional carriers or excipients described above can also be added in the mixture. Exemplary methods of preparation include dry powder blending, wet granulation, dry granulation by compaction/slugging, spray drying, hot melt extrusion, extrusion spheronization and fluidized bed granulation. As described above, in order to have good uniformity, the active ingredient and all the excipients in the powder formulation should have suitable particle size range and need to pass certain mesh before using, such as mesh 20, 40, 60, 80 or 100.

In exemplary embodiments, the method includes the following steps:
(a) mixing tadalafil or a pharmaceutically acceptable salt thereof with a first portion of glidant to obtain a first mixture; and
(b) mixing the first mixture with one or more additional excipients.

In some embodiments, the method further includes mixing the first mixture with a first portion of diluent prior to step (b). Preferably, the glidant, diluent and/or other ingredients/excipients is passed through mesh of suitable size. In some embodiments, the one or more additional excipients include a second portion of glidant and/or a second portion of diluent. In some embodiments, the method further includes mixing the first mixture, during step (b) or after step (b) with a second portion of the glidant and/or a second portion of diluent. In some embodiments, the glidant is silicon dioxide. In some embodiments, the diluent is sorbitol. In some embodiments, the ratio between the first portion of glidant and the second portion of glidant ranges from about 1:2 to about 1:5, from about 1:2 to about 1:4, or from about 1:3 to about 1:4. In some embodiments, the ratio between the first portion of diluent and the second portion of diluent ranges from about 1:1 to about 1:2, including for example from about 1:1.2, about 1:1.4, about 1:1.6 or about 1:1.8.

Another aspect of the patent document provides a method of treating a disease or condition using the powder formulation or the suspension described above. The powder formulation needs to be reconstituted into a suspension. The suspension contains for example, 5 mg/ml of tadalafil (or a pharmaceutically acceptable salt thereof or a derivative thereof) for oral administration to a subject in need. Examples of the disease or condition include erectile dysfunction, Benign Prostatic Hyperplasia and pulmonary arterial hypertension. Other exemplary applications include treatment of Heart failure, hypertension, Left ventricle diastolic dysfunction, scleroderma spectrum of disease, Systemic Sclerosis, Raynaud's, fetal growth restriction, Mountain Sickness, Skeletal Muscle and Perceptual Fatigue, Interstitial Lung Disease of Scleroderma, Chronic Obstructive Pulmonary Disease, Duchenne Muscular Dystrophy.

EXAMPLES

Example 1

Figure 1:
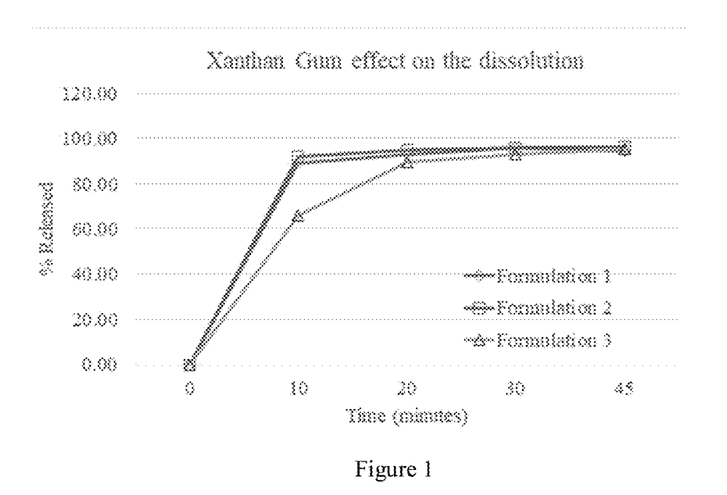
FIG. 1 shows the effect of xanthan gum percentage on dissolution of an exemplary formulation.
Figure 2:
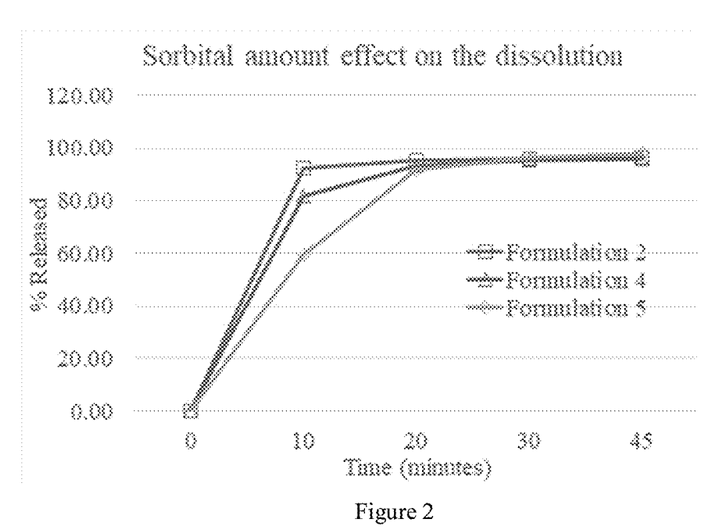
FIG. 2 shows the effect of sorbitol percentage on dissolution of an exemplary formulation.

Formulation compositions of tadalafil powder for oral suspension, formulation 1-5, were prepared and are shown in table 1. The dissolution of these formulation is shown in FIGS. 1 and 2.

TABLE 1

| Formulation compositions of tadalafil powder for oral suspension | | | | | |
| --- | --- | --- | --- | --- | --- |
| Description | Formulation 1 % w/w (powder) | Formulation 2 % w/w (powder) | Formulation 3 % w/w (powder) | Formulation 4 % w/w (powder) | Formulation 5 % w/w (powder) |
| Tadalafil | 4.28 | 4.28 | 4.28 | 3.20 | 2.14 |
| Sucralose | 2.14 | 2.14 | 2.14 | 1.60 | 1.07 |
| Xanthan gum | 2.57 | 3.43 | 4.28 | 2.56 | 1.71 |

TABLE 1-continued

Formulation compositions of tadalafil powder for oral suspension

| Description | Formulation 1 % w/w (powder) | Formulation 2 % w/w (powder) | Formulation 3 % w/w (powder) | Formulation 4 % w/w (powder) | Formulation 5 % w/w (powder) |
|---|---|---|---|---|---|
| Colloidal silicon dioxide | 2.5 | 2.5 | 2.5 | 1.87 | 1.25 |
| Sorbitol | 78.16 | 77.3 | 76.45 | 83.06 | 88.65 |
| Citric acid anhydrous | 6 | 6 | 6 | 4.48 | 3 |
| Sodium citrate dihydrate | 3.5 | 3.5 | 3.5 | 2.61 | 1.75 |
| Sodium benzoate | 0.86 | 0.86 | 0.86 | 0.64 | 0.43 |
| Total | 100 | 100 | 100 | 100 | 100 |

The viscosity of suspension after reconstitution of formulation 1, 2 and 3 are 144, 698.7 and 749 cp respectively. Formulation 1 has the low viscosity, where formulation 3 has the high viscosity and slower dissolution rate (FIG. 1).

TABLE 2

The effect of sorbitol percentage on powder BU, suspension viscosity and dissolution

| | Formulation 2 | Formulation 4 | Formulation 5 |
|---|---|---|---|
| Sorbitol percentage | 77.3% | 82.86% | 88.86% |
| Blend uniformity (BU), AV value | 4.8 | 12.6 | 21.1 |
| Viscosity | 688 cp | 701.3 cp | 760 cp |
| Dissolution at 10 min | 92.13% | 81.59% | 59.33% |

The effect of sorbitol percentage is shown in table 2. Higher sorbitol percentage in the formulation results in worse blend uniformity (higher AV value), higher viscosity and lower dissolution rate (FIG. 2).

TABLE 3

Formulation compositions of tadalafil powder for oral suspension with different percentage of silicon dioxide

| Description | Formulation 6 % w/w (powder) | Formulation 7 % w/w (powder) | Formulation 8 % w/w (powder) | Formulation 9 % w/w (powder) | Formulation 10 % w/w (powder) |
|---|---|---|---|---|---|
| Tadalafil | 4.28 | 4.28 | 4.17 | 4.14 | 4.09 |
| Sucralose | 2.14 | 2.14 | 1.04 | 1.03 | 1.02 |
| Xanthan gum | 3.43 | 3.43 | 1.67 | 1.65 | 1.63 |
| Colloidal silicon dioxide | 1.5 | 0.57 | 0.49 | 1.21 | 2.35 |
| Sorbitol | 78.3 | 79.23 | 87.61 | 86.97 | 85.96 |
| Citric acid anhydrous | 6 | 6 | 2.92 | 2.89 | 2.86 |
| Sodium citrate dihydrate | 3.5 | 3.5 | 1.70 | 1.69 | 1.67 |
| Sodium benzoate | 0.86 | 0.86 | 0.42 | 0.41 | 0.41 |
| Total solids | 100 | 100 | 100 | 100 | 100 |
| Blend uniformity, AV value | 12.8 | 28.4 | 14.54 | 6.44 | 4.78 |

Formulation compositions of tadalafil powder for oral suspension with different percentage of silicon dioxide is shown in table 3. The data comparing within group 1 (Formulation 2, 6 and 7) or within group 2 (Formulation 8, 9 and 10) shows that higher silicon dioxide percentage in the formulation results in better blend uniformity (lower AV value). However, too much silicon dioxide (>3%) in the formulation will make the process difficult.

The preparation step of tadalafil powder for oral suspension was as following:

1. API was mixed with Colloidal silicon dioxide ($SiO_2$) (part 1) for 10 min (20 rpm)
2. Sorbitol (part 1) also pass through the Comil for de-lumping
3. The API-SiO2 mixture and Sorbitol 1 were mixed in the blender for 5 min (20 rpm) and then pass through the Comil
4. All other milled excipients (including SiO2 part 2 and Sorbitol part 2) were added and mixed in the blend for 10 min (20 rpm) to form the final blend.

API need to be mixed with partial Colloidal silicon dioxide (SiO2) first, without this step, the final formulation has the low assay (89.9%) and poor blend uniformity.

Various techniques can be employed in the preparation, including for example, dry powder blending, wet granulation, dry granulation by compaction or slugging, spray drying, hot melt extrusion, extrusion spheronization and fluidized bed granulation.

Tadalafil powder for oral suspension was reconstituted to form 5 mg/ml suspension. The assay of suspension in the up, middle and bottom position are 99.8%, 99.0% and 99.7% respectively, which indicate that the homogeneity of suspension was acceptable. The viscosity of suspension was ~688 cp.

Figure 3:
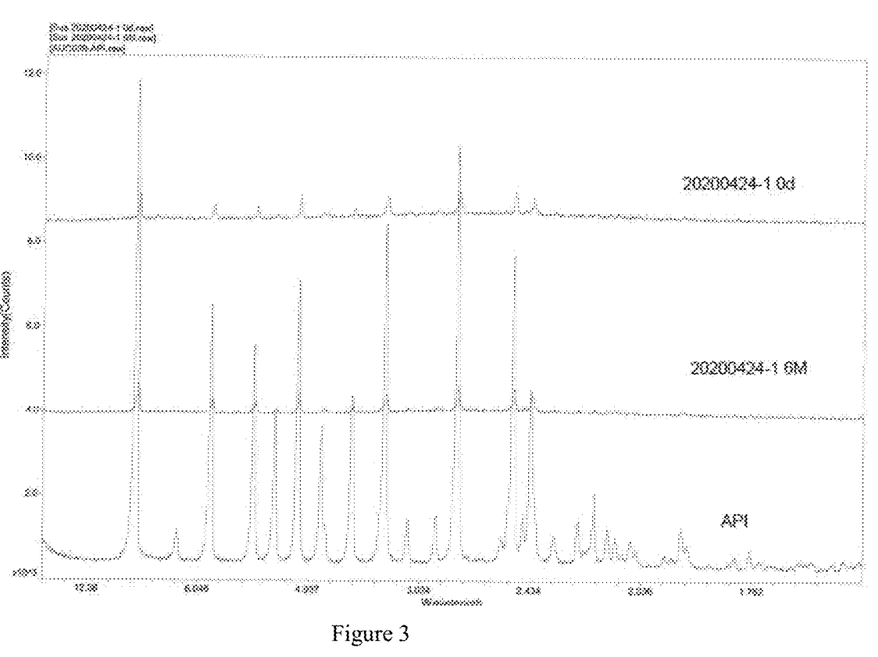
FIG. 3 shows physical stability of suspension after reconstitution of an exemplary formulation.

The reconstituted tadalafil suspension was stirred to evaluate the physical and chemical stability. The crystalline form of tadalafil was unchanged after 6 months (FIG. 3), and no additional impurity was observed, indicating that reconstituted suspension has the good physical and chemical stability.

Tadalafil oral suspension were also prepared and formulation compositions are shown in table 4. The suspension is physically and chemically stable and has an in vitro release of at least about 75% of the tadalafil within about 10 minutes under USP dissolution apparatus 2 in 1000 ml of 0.5% SLS at 50 rpm.

TABLE 4

Formulation compositions of tadalafil oral suspension

| Description | Formulation 11 (suspension) mg/ml | Formulation 12 (suspension) mg/ml |
|---|---|---|
| Tadalafil | 5 | 10 |
| Sucralose | 2.5 | 2.5 |
| Xanthan gum | 4 | 4 |
| Colloidal silicon dioxide | 2.92 | 2.92 |
| Sorbitol | 90.25 | 210.33 |
| Citric acid anhydrous | 7 | 7 |
| Sodium citrate dihydrate | 4.08 | 4.08 |
| Sodium benzoate | 1 | 1 |
| Viscosity (cp) | 688 cp | 733 cp |

It will be appreciated by persons skilled in the art that fibers described herein are not limited to what has been particularly shown and described. Rather, the scope of the formulation, the suspension and the method are defined by the claims which follow. It should further be understood that the above description is only representative of illustrative examples of embodiments. The description has not attempted to exhaustively enumerate all possible variations. The alternate embodiments may not have been presented for a specific component of the formulation or step of the method, and may result from a different combination of described components/excipients or steps, or that other un-described alternate embodiments may be available for a component/excipient or a step, is not to be considered a disclaimer of those alternate embodiments. It will be appreciated that many of those un-described embodiments are within the literal scope of the following claims, and others are equivalent.

The invention claimed is:

1. A powder formulation suitable for reconstitution with a pharmaceutically acceptable carrier to form a stable suspension oral dosage form comprising:
   tadalafil or a pharmaceutically acceptable salt;
   a suspending agent in an amount ranging from about 1% to about 5% w/w in the powder formulation, wherein the suspending agent is selected from the group consisting of hydrocolloid gum, cellulosic derivative, a polysaccharide, alginate, acrylic acid copolymer, polyvinylpyrrolidone, aluminium magnesium silicate, and any combination thereof;
   a glidant in an amount ranging from about 1% to about 3.0% w/w of the powder formulation;
   a sorbitol in an amount ranging from about 70% to about 80% w/w of the powder formulation; and
   one or more pharmaceutically acceptable excipients,
   wherein the tadalafil or the pharmaceutically acceptable salt thereof and the suspending agent have a ratio ranging from about 10:1 to about 5:8 by weight;
   wherein the suspending agent, the one or more pharmaceutically acceptable excipients, and their respective amounts are selected so that the ratio of area under curve (AUC 0-inf) between tadalafil suspension to tadalafil in immediate release tablet form with the same dose ranges from about 0.8 to about 1.25 after oral administration; and
   wherein the suspending agent, the one or more pharmaceutically acceptable excipients, and their respective amounts are selected so that the ratio of a maximum tadalafil plasma concentration ($C_{max}$) between tadalafil suspension to tadalafil in immediate release tablet form with the same dose ranges from about 0.75 to about 0.90 after oral administration.

2. The powder formulation of claim 1, wherein the suspending agent, the one or more pharmaceutically acceptable excipients, and their respective amounts are selected so that less than about 1% of the tadalafil or the pharmaceutically acceptable salt thereof decomposes for 3 months after the powder formulation is reconstituted into the suspension.

3. The powder formulation of claim 1, wherein the tadalafil or the pharmaceutically acceptable salt thereof and the suspending agent have a ratio of about 5:4 by weight.

4. The powder formulation of claim 1, wherein the suspending agent is hydrocolloid gum.

5. The powder formulation of claim 1, wherein the suspending agent is xanthan gum.

6. The powder formulation of claim 1, wherein the suspending agent and its amount are selected so that the reconstituted suspension maintains a sedimentation ratio of more than 0.9 in a sitting, non-stirred condition for at least 24 hours.

7. The powder formulation of claim 1, wherein the glidant is selected from the group consisting of silicon dioxide, starch, talc and any combination thereof.

8. The powder formulation of claim 1, where the glidant is silicon dioxide.

9. The powder formulation of claim 1, wherein the suspending agent, the one or more pharmaceutically acceptable excipients, and their respective amounts are selected so that the suspension provides an in vitro release of at least 75% of the tadalafil within about 10 minutes under USP dissolution apparatus 2 in 1000 ml of 0.5% SLS at 50 rpm.

10. The powder formulation of claim 1, wherein the suspending agent, the one or more pharmaceutically acceptable excipients, and their respective amounts are selected so that the suspension prepared from the powder formulation provides a release of the tadalafil bioequivalent to the same dose of tadalafil in immediate release tablet form.

11. The powder formulation of claim 1, wherein the suspending agent, the one or more pharmaceutically acceptable excipients, and their respective amounts are selected so that the plasma concentration profile at steady state is characterized by a maximum tadalafil plasma concentration to average plasma concentration ratio (Cmax/Cave) ranging from about 1.4 to about 1.9 after administration.

12. The powder formulation of claim 1, wherein the suspending agent, the one or more pharmaceutically acceptable excipients, and their respective amounts are selected so that the plasma concentration profile at steady state is characterized by a minimum tadalafil plasma concentration to average plasma concentration ratio (Cmin/Cave) ranging from about 0.6 to about 0.7 after administration.

13. The powder formulation of claim 1, wherein the tadalafil or the pharmaceutically acceptable salt thereof has a D90 ranging from about 1 μm to about 20 μm prior to being mixed with the suspending agent.

14. The powder formulation of claim 1, further comprising a diluent selected from the group consisting of sucrose, dextrose, mannitol, sorbitol, maltitol, starch, lactose, microcrystalline cellulose, and any combination thereof, wherein the diluent ranges from about 10% to about 98% by weight of the powder formulation.

15. The powder formulation of claim 1, which further comprises sorbitol ranging from about 50% to about 85% by weight in the powder formulation.

16. The powder formulation of claim 1, which further comprises sorbitol ranging from about 70% to about 85%.

17. The powder formulation of claim 1, further comprising a buffering agent selected from the group consisting of sodium citrate, citric acid, fumaric acid, tartaric acid, potassium citrate, sodium bicarbonate, potassium bicarbonate, sodium dihydrogen phosphate, disodium hydrogen phosphate, sodium hydroxide, potassium dihydrogen phosphate and any combination thereof.

18. The powder formulation of claim 1, wherein the suspending agent, the one or more pharmaceutically acceptable excipients, and their respective amounts are selected so that the suspension has a pH in the range of 2 to 6 after the powder formulation is reconstituted into the suspension.

19. A method of treating a disease comprising administering the powder formulation of claim 1 to a subject in need, wherein the disease is selected from the group consisting of erectile dysfunction, enlarged prostate, pulmonary arterial hypertension and Duchenne Muscular Dystrophy.

* * * * *